United States Patent [19]

Maurer et al.

[11] 4,159,323

[45] * Jun. 26, 1979

[54] O,O'-DIALKYL-4,6-DIPHOSPHORYLATED PYRIMIDINES AND COMPOSITIONS AND METHODS FOR COMBATING ARTHROPODS CONTAINING THEM

[75] Inventors: Fritz Maurer; Hans-Jochem Riebel, both of Wuppertal-1; Ingeborg Hammann, Cologne; Wolfgang Behrenz, Overath, all of Fed. Rep. of Germany

[73] Assignee: Bayer Aktiengesellschaft, Leverkusen, Fed. Rep. of Germany

[*] Notice: The portion of the term of this patent subsequent to Nov. 22, 1994, has been disclaimed.

[21] Appl. No.: 790,378

[22] Filed: Apr. 25, 1977

[30] Foreign Application Priority Data

May 3, 1976 [DE] Fed. Rep. of Germany ....... 2619450

[51] Int. Cl.² ............................ A01N 9/36; C07F 9/65
[52] U.S. Cl. .................................... 424/200; 544/243
[58] Field of Search ..................... 260/251 P, 256.4 E, 260/256.5 R; 424/200; 544/243

[56] References Cited

U.S. PATENT DOCUMENTS

| 3,216,894 | 11/1965 | Lorenz et al. ........................ 424/200 |
| 3,309,371 | 3/1967 | Curry et al. ........................... 260/925 |
| 3,547,920 | 12/1970 | Fest et al. ........................ 260/250 AP |
| 4,059,696 | 11/1977 | Maurer et al. ........................ 424/200 |
| 4,107,301 | 8/1978 | Hofer et al. ........................... 424/200 |

FOREIGN PATENT DOCUMENTS 95490 2/1973 German Democratic Rep.

OTHER PUBLICATIONS

Reznik et al., Chemical Abstracts, vol. 79. 42,445k (1973).

Primary Examiner—Donald G. Daus
Assistant Examiner—Diana G. Rivers
Attorney, Agent, or Firm—Sprung, Felfe, Horn, Lynch & Kramer

[57] ABSTRACT

O,O'-Dialkyl-4,6-diphosphorylated pyrimidines of the formula

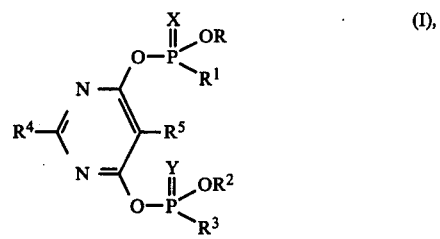

in which
R and $R^2$ each independently is alkyl,
$R^1$ and $R^3$ each independently is alkyl, alkoxy, alkylthio, alkylamino or phenyl,
$R^4$ is hydrogen, alkyl, alkoxy, alkylthio or dialkylamino,
$R^5$ is hydrogen, halogen or alkyl, and
X and Y each independently is oxygen or sulfur, with the proviso that at least one of the radicals, R, $R^1$, $R^2$ and $R^3$ must be different from the others or that X must be different from Y, which possess arthropodicidal and nematicidal properties.

10 Claims, No Drawings

O,O'-DIALKYL-4,6-DIPHOSPHORYLATED PYRIMIDINES AND COMPOSITIONS AND METHODS FOR COMBATING ARTHROPODS CONTAINING THEM

The present invention relates and and has for its objects the provision of particular new O,O'-dialkyl-4,6-diphosphorylated pyrimidines which possess arthropodicidal and nematicidal properties, active compositions in the form of mixtures of such compounds with solid and liquid dispersible carrier vehicles, and methods for producing such compounds and for using such compounds in a new way especially for combating pests, e.g., insects, acarids and nematodes, with other and further objects becoming apparent from a study of the within specification and accompanying examples.

It is known from U.S. Pat. No. 2,754,243, German Published DAS Nos. 1,170,401 and 1,197,878 and published Netherlands patent application No. 6,713,142 that monophosphorylated pyrimidines, for example O,O-diethyl-O-[2-methylthio-(Compound A) and 2-isopropyl-6-methyl-pyrimidin-(4)yl]-thionophosphoric acid ester (Compound B), and bis-(thionophosphoric acid ester)-diphenylsulfides and -di-sulfides, for example O,O,O',O'-tetraethyl-O,O'-thio-(Compound C) and -dithio-di-p-phenylene-thionophosphoric acid ester (Compound D), possess insecticidal and acaricidal properties.

The present invention now provides, as new compounds, the diphosphorylated pyrimidines of the general formula

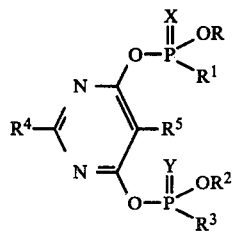

in which
R and $R^2$ each independently is alkyl,
$R^1$ and $R^3$ each independently is alkyl, alkoxy, alkylthio, alkylamino or phenyl,
$R^4$ is hydrogen, alkyl, alkoxy, alkylthio or dialkylamino,
$R^5$ is hydrogen, halogen or alkyl, and
X and Y each independently is oxygen or sulfur, with the proviso that at least one of the radicals, R, $R^1$, $R^2$ and $R^3$ must be different from the others or that X must be different from Y, Preferably, R and $R^2$, which may be identical or different, each represent straight-chain or branched alkyl with 1 to 4 carbon atoms, $R^1$ and $R^3$, which may be identical or different, each represent straight-chain or branched alkyl, alkoxy, alkylthio or monoalkylamino with in each case 1 to 4 carbon atoms or phenyl, $R^4$ represents hydrogen, straight-chain or branched alkyl with 1 to 4 carbon atoms or straight-chain or branched alkoxy, alkylthio or dialkylamino each with 1 to 3 carbon atoms per alkyl radical, $R^5$ represents hydrogen, chlorine, bromine or straight-chain or branched alkyl with 1 to 3 carbon atoms and X and Y each represent sulfur.

Surprisingly, the diphosphorylated pyrimidines according to the invention exhibit a better insecticidal and acaricidal action than the corresponding previously known compounds of similar structure and of the same type of action. The products of the present invention thus represent a genuine enrichment of the art.

The present invention also provides a process for the preparation of a diphosphorylated pyrimidine of the formula (I) in which an O-[6-hydroxypyrimidin(4)yl]-(thiono)(thiol)-phosphoric(phosphonic) acid ester or ester-amide of the general formula

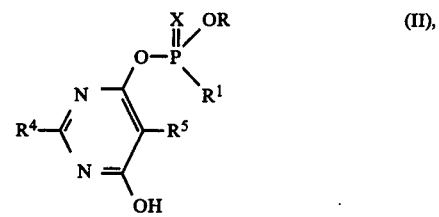

in which
R, $R^1$, $R^4$, $R^5$ and X have the meanings mentioned above, is reacted, either in the form of an alkali metal salt, alkaline earth metal salt or ammonium salt thereof or as such in the presence of an acid acceptor, if appropriate in the presence of a solvent or diluent, with a (thiono)(thiol)phosphoric(phosphonic) acid ester halide or ester-amide halide of the general formula

in which
$R^2$, $R^3$ and Y have the abovementioned meanings and Hal represents halogen, preferably chlorine.

If, for example, O-[2-ethylthio-5-chloro-6-hydroxypyrimidin(4)yl]-O-ethyl-N-iso-propyl-thionophosphoric acid diester-amide and O-iso-propyl-ethanephosphonic acid ester chloride are used as starting materials, the course of the reaction can be represented by the following equation:

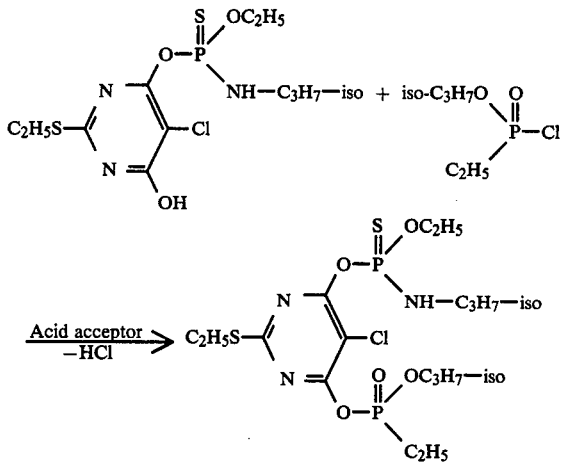

The O-[6-hydroxy-pyrimidin(4)yl]-(thiono)(thiol)-phosphoric (phosphonic) acid esters and ester-amides (II) to be used as starting materials can be prepared in accordance with generally customary processes described in the literature, for example by reacting 4,6-dihydroxypyrimidines with (thiono)(thiol)phosphoric(-phosphonic) acid ester halides or ester-amide halides, if appropriate in the presence of acid acceptors and, if appropriate, in the presence of a solvent, in accordance with the following equation:

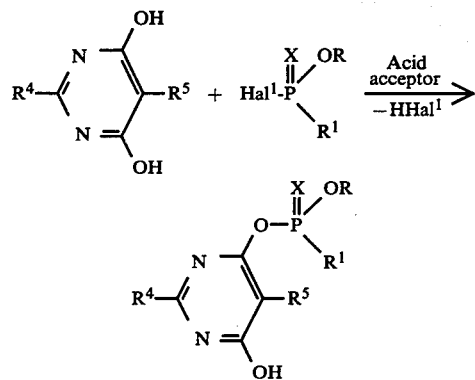

wherein

R, $R^1$, $R^4$, $R^5$ and X have the abovementioned meanings and $Hal^1$ represents halogen, preferably chlorine.

The following may be mentioned as individual examples: O-[6-hydroxy-pyrimidin(4)yl]-, O-[6-hydroxy-2-methylpyrimidin(4)yl]-, O-[6-hydroxy-2-ethyl-pyrimidin(4)yl]-, O-[6-hydroxy-2-n-propyl-pyrimidin(-4)yl], O-[6-hydroxy-2-iso-propyl-pyrimidin(4)yl]-, O-[6-hydroxy-2-n-butylpyrimidin(4)yl]-, O-[6-hydroxy-2-sec.-butyl-pyrimidin(4)yl]-, O-[6-hydroxy-2-iso-butyl-pyrimidin(4)yl]-, O-[6-hydroxy-2-methoxy-pyrimidin(-4)yl]-, O-[6-hydroxy-2-ethoxy-pyrimidin(4) yl]-, O-[6-hydroxy-2-n-propoxy-pyrimidin(4)yl]-, O-[6-hydroxy-2-iso-propoxy-pyrimidin(4)yl]-, 6-[6-hydroxy-2-methylthio-pyrimidin(4)yl]-, O-[6-hydroxy-2-ethylthiopyrimidin(4)yl]-, O-[6-hydroxy-2-n-propylthio-pyrimidin(4)yl]-, O-[6-hydroxy-2-iso-propylthio-pyrimidin(4)yl]-, O-[6-hydroxy-2-dimethylamino-pyrimidin(4)yl]-, O-[6-hydroxy-2-diethylamino-pyrimidin(4)yl]-, O-[6-hydroxy-2-di-n-propylaminopyrimidin(4)yl]-, O-[6-hydroxy-5-chloro-pyrimidin(4)yl]-, O-[6-hydroxy-5-bromo-pyrimidin(-4)yl]-, O-[6-hydroxy-5-methyl-pyrimidin(4)yl]-, O-[6-hydroxy-5-ethyl-pyrimidin (4)yl]-, O-[6-hydroxy-5-n-propyl-pyrimidin(4)yl]-, O-[6-hydroxy-5-iso-propyl-pyrimidin(4)yl]-, O-[6-hydroxy-2-methyl-5-chloro-pyrimidin(4)yl]-, O-[6-hydroxy-2-ethyl-5-chloro-pyrimidin(4)yl]-, O-[6-hydroxy-2-n-propyl-5-chloro-pyrimidin(4)yl]-, O-[6-hydroxy-2-iso-propyl-5-chloro-pyrimidin(4)yl]-, O-[6-hydroxy-2-methoxy-5-chloro-pyrimidin(4)yl]-, O-[6-hydroxy-2-ethoxy-5-chloro-pyrimidin(4)yl]-, O-[6-hydroxy-2-methylthio-5-chloro-pyrimidin(4)yl]-, O-[6-hydroxy-2-ethylthio-5-chloro-pyrimidin(4)yl]-, O-[6-hydroxy-2-dimethylamino-5-chloro-pyrimidin(4)yl]-, O-[6-hydroxy-2-diethylamino-5-chloro-pyrimidin(4)yl]-, O-[6-hydroxy-2-methyl-5-bromo-pyrimidin(4)yl]-, O-[6-hydroxy-2-ethyl-5-bromo-pyrimidin(4)yl]-, O-[6-hydroxy-2-n-propyl-5-bromo-pyrimidin(4)yl]-, O-[6-hydroxy-2-isopropyl-5-bromo-pyrimidin(4)yl-, O-[6-hydroxy-2-methoxy-5-bromo-pyrimidin(4)yl]-, O-[6-hydroxy-2-ethoxy-5-bromo-pyrimidin(4)yl]-, O-[6-hydroxy-2-methylthio-5-bromo-pyrimidin(4)yl]-, O-[6-hydroxy-2-ethylthio-5-bromo-pyrimidin(4)yl]-, O-[6-hydroxy-2-dimethylamino-5-bromo-pyrimidin(4)yl]-, O-[6-hydroxy-2-diethylamino-5-bromo-pyrimidin(4)yl]-, O-[6-hydroxy-2-methyl-5-methyl-pyrimidin(4)yl-, O-[6-hydroxy-2-ethyl-5-methyl-pyrimidin(4)yl]-, O-[6-hydroxy-2-n-propyl-5-methyl-pyrimidin(4)yl]-, O-[6-hydroxy-2-isopropyl-5-methyl-pyrimidin(4)yl]-, O-[6-hydroxy-2-methoxy-5-methyl-pyrimidin(4)yl]-, O-[6-hydroxy-2-ethoxy-5-methyl-pyrimidin(4)yl]-, O-[6-hydroxy-2-methylthio-5-methyl-pyrimidin(4)yl]-, O-[6-hydroxy-2-ethylthio-5-methyl-pyrimidin(4)yl]-, O-[6-hydroxy-2-dimethylamino-5-methyl-pyrimidin(4)yl]-, O-[6-hydroxy-2-diethylamino-5-methyl-pyrimidin(4)yl]-, O-[6-hydroxy-2-methyl-5-ethyl-pyrimidin(4)yl]-, O-[6-hydroxy-2-ethyl-5-ethyl-pyrimidin(4)yl]-, O-[6-hydroxy-2-n-propyl-5-ethyl-pyrimidin(4)yl]-, O-[6-hydroxy-2-iso-propyl-5-ethyl-pyrimidin(4)yl]-, O-[6-hydroxy-2-methoxy-5-ethyl-pyrimidin(4)yl]-, O-[6-hydroxy-2-ethoxy-5-ethyl-pyrimidin(4)yl]-, O-[6-hydroxy-2-methylthio-5-ethyl-pyrimidin(4)yl]-, O-[6-hydroxy-2-ethylthio-5-ethyl-pyrimidin(4)yl]-, O-[6-hydroxy-2-dimethylamino-5-ethyl-pyrimidin(4)yl]-, O-[6-hydroxy-2-diethylamino-5-ethyl-pyrimidin(4)yl]-, O-[6-hydroxy-2-methyl-5-n-propyl-pyrimidin(4)yl]-, O-[6-hydroxy-2-ethyl-5-n-propyl-pyrimidin(4)yl]-, O-[6-hydroxy-2-n-propyl-5-n-propyl-pyrimidin(4)yl]-, O-[6-hydroxy-2-iso-propyl-5-n-propyl-pyrimidin(4)yl]-, O-[6-hydroxy-2-methoxy-5-n-propyl-pyrimidin(4)yl]-, O-[6-hydroxy-2-ethoxy-5-n-propyl-pyrimidin(4)yl]-, O-[6-hydroxy-2-methylthio-5-n-propyl-pyrimidin(4)yl]-, O-[6-hydroxy-2-ethylthio-5-n-propyl-pyrimidin(4)yl]-, O-[6-hydroxy-2-dimethylamino-5-n-propyl-pyrimidin(-4)yl]-, O-[6-hydroxy-2-diethylamino-5-n-propyl-pyrimidin(4)yl]-O,O-dimethyl-, -O,O-diethyl-, -O,O-di-n-propyl-, -O,O-di-iso-propyl-, -O,O-di-n-butyl-, -O,O-di-isobutyl-, -O,O-di-sec.-butyl-, -O-methyl-O-ethyl-, -O-methyl-O-n-propyl-, -O-methyl-O-iso-propyl-, -O-methyl-O-n-butyl-, -O-methyl-O-iso-butyl-, -O-methyl-O-sec.-butyl-, -O-methyl-O-tert.-butyl-, -O-ethyl-O-n-propyl-, -O-ethyl-O-iso-propyl-, -O-ethyl-O-n-butyl-, -O-ethyl-O-sec.-butyl-, -O-ethyl-O-iso-butyl-, -O-n-propyl-O-butyl- and -O-iso-propyl-O-butyl-thionophosphoric acid ester, as well as -O,S-dimethyl-, -O,S-diethyl-, -O,S-di-n-propyl-, -O,S-di-iso-propyl-, -O,S-di-n-butyl-, -O,S-di-iso-butyl-, -O,S-di-tert.-butyl-, -O-ethyl-S-n-propyl-, -O-ethyl-S-iso-propyl-, -O-ethyl-S-n-butyl-, -O-ethyl-S-sec.-butyl-, -O-n-propyl-S-ethyl-, -O-n-propyl-S-iso-propyl-, -O-n-butyl-S-n-propyl- and -O-sec.-butyl-S-ethyl-thionothiolphosphoric acid ester and -O-methyl-, -O-ethyl-, -O-n-propyl-, -O-iso-propyl-, -O-n-butyl-, -O-iso-butyl-, -O-sec.-butyl- and -O-tert.-butyl-methane-, -ethane-, -n-propane-, -iso-propane-, -n-butane-, -iso-butane-, -tert.-butane-, -sec.-butane- and -benzene-thionophosphonic acid diester, and -O-methyl-N-methyl-, -O-methyl-N-ethyl-, -O-methyl-N-n-propyl-, -O-ethyl-N-methyl-, -O-ethyl-N-ethyl-, -O-ethyl-N-n-propyl-, -O-ethyl-N-iso-propyl-, -O-n-propyl-N-methyl-, -O-n-propyl-N-ethyl, -O-n-propyl-N-n-propyl, -O-n-propyl-N-iso-propyl-, -O-iso-propyl-N-methyl-, -O-iso-propyl-N-ethyl-, -O-iso-propyl-N-n-butyl- and -O-n-butyl-N-n-butyl-thionophosphoric acid diester amide.

The (thiono)(thiol)phosphoric(phosphonic) acid ester halides and ester-amide halides (III) which are also to be used as starting materials are known and can be prepared in accordance with processes described in the literature. The following may be mentioned as individual examples of these compounds: O,O-dimethyl-, O,O-diethyl-, O,O-di-n-propyl-, O,O-di-iso-propyl-, O,O-din-butyl-, O,O-di-iso-butyl-, O,O-disec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-phosphoric acid diester halides and the corresponding thiono analogues; O,S-dimethyl-, O,S-diethyl-, O,S-di-n-propyl-, O,S-di-iso-propyl-, O,S-di-n-butyl-, O,S-di-iso-butyl-, O,S-di-tert.-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethyl-thiolphosphoric acid diester halides and the corresponding thiono analogues; O-methyl-, O-ethyl-, O-n-propyl-, O-iso-propyl-, O-n-butyl-, O-iso-butyl-, O-sec.-butyl- and O-tert.-butyl-methane-, ethane-, n-propane-, isopropane, n-butane-, isobutane-, tert.-butane-, sec.-butane- and -benzene-phosphonic acid ester halides and the corresponding thiono analogues; and O-methyl-N-methyl-, O-methyl-N-ethyl-, O-methyl-N-n-propyl-, O-methyl-N-iso-propyl-, O-methyl-N-n-butyl-, O-methyl-N-sec.-butyl-, O-methyl-N-iso-butyl-, O-ethyl-N-methyl-, O-ethyl-N-ethyl-, O-ethyl-N-n-propyl-, O-ethyl-N-iso-propyl-, O-ethyl-N-n-butyl-, O-ethyl-N-isobutyl-, O-ethyl-N-sec.-butyl-, O-n-propyl-N-methyl-, O-n-propyl-N-ethyl-, O-n-propyl-N-n-propyl-, O-n-propyl-N-iso-propyl-, O-n-propyl-N-n-butyl-, O-n-propyl-N-iso-butyl-, O-n-propyl-N-sec.-butyl-, O-iso-propyl-N-methyl-, O-iso-propyl-N-ethyl-, O-iso-propyl-N-n-propyl-, O-iso-propyl-N-iso-propyl-, O-iso-propyl-N-n-butyl-, O-iso-propyl-N-iso-butyl- O-iso-propyl-N-sec.-butyl-, O-n-butyl-N-methyl-, O-n-butyl-N-ethyl-, O-n-butyl-N-n-propyl-, O-n-butyl-N-iso-propyl-, O-n-butyl-N-n-butyl-, O-iso-butyl-N-ethyl-, O-iso-butyl-N-iso-propyl- and O-iso-butyl-N-n-propyl-phosphoric acid ester-amide halides and the corresponding thiono analogues.

The process for the preparation of the compounds according to the invention is preferably carried out in the presence of a suitable solvent or diluent. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C., preferably at 35° to 60° C.

In general, the reaction is allowed to take place under normal pressure.

To carry out the process, the starting components are preferably employed in equimolar amounts. An excess of one or other component produces no essential advantages. The reactants are in general brought together in one of the stated solvents and are stirred for one or more hours, in most cases at an elevated temperature, to complete the reaction. Thereafter, an organic solvent, for example toluene, is added and the organic phase is worked up in the usual manner by washing, drying and distilling off the solvent.

The new compounds are obtained in the form of oils which in most cases cannot be distilled without decomposition but are freed from the last volatile constituents by so-called "slight distillation," that is to say be prolonged heating under reduced pressure to moderately elevated temperatures, and are purified in this manner. They are characterized by the refractive index.

As already mentioned, the diphosphorylated pyrimidines according to the invention are distinguished by an excellent insecticidal and acaricidal activity. They are active against plant pests, pests harmful to health and pests of stored products. They combine a low phytotoxicity with a good action against both sucking and biting insects and mites.

For this reason, the compounds according to the invention can be employed successfully as pesticides in plant protection and in the hygiene field and the field of protection of stored products.

The active compounds are well tolerated by plants, have a favorable level of toxicity to warm-blooded animals, and can be used for combating arthropod pests, especially insects and arachnids, and nematode pests which are encountered in agriculture, in forestry, in the protection of stored products and of materials, and in the hygiene field. They are active against normally sensitive and resistant species and against all or some stages of development. The above-mentioned pests include: from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of to Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trihodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus ssp. and Psylla spp., from the order of the Lepidoptera, for example *Pectinophora*

*gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus holoeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp, Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, dichlorodifluoromethane, trichlorofluoromethane, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g., surface-active agents, for this purpose: emulsifying agents, such as non-ionic and/or anionic emulsifying agents (e.g., polyethylene oxides esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides and acaricides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g., average particle diameter of from 50–100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g., about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g., arthropods and nematodes, which comprises applying to at least one of correspondingly (a) such arthropods, (b) such nematodes and (c) the corresponding habitat thereof, i.e., the locus to be protected, e.g., to a growing crop, to an area where a crop is to be grown or to a domestic animal, a correspondingly combative or toxic amount, i.e., an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella Test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% meant that all the caterpillars were killed, whereas 0% meant that none of the caterpillars were killed.

The active compounds, the concentrations of the active compounds, the evaluation times and the results can be seen from Table 1:

Table 1

(Plutella test)

| Active compound | Active compound concentration in % | Degree of destruction on % after 3 days |
|---|---|---|
| ![structure A: pyrimidine with CH3S, CH3, N=, and O–P(=S)(OC2H5)2 substituents] (known) (A) | 0.1<br>0.01 | 100<br>0 |
| ![structure: pyrimidine with iso-C3H7, N=, and O–P(=S)(OCH3)2 substituents] (6) | 0.1<br>0.01 | 100<br>90 |

Table 1-continued
(Plutella test)

| Active compound | Active compound concentration in % | Degree of destruction on % after 3 days |
|---|---|---|
| (9) iso-$C_3H_7$-pyrimidine with O-P(S)(OC$_2$H$_5$)$_2$ and O-P(S)(OC$_2$H$_5$)(phenyl) | 0.1<br>0.01 | 100<br>100 |
| (4) iso-$C_3H_7$-pyrimidine with O-P(S)(OC$_2$H$_5$)$_2$ and O-P(S)(OC$_2$H$_5$)(SC$_3$H$_7$-n) | 0.1<br>0.01 | 100<br>100 |
| (21) (CH$_3$)$_2$N-pyrimidine with O-P(S)(OC$_2$H$_5$)$_2$ and O-P(S)(OC$_2$H$_5$)(C$_2$H$_5$) | 0.1<br>0.01 | 100<br>100 |
| (20) C$_2$H$_5$O-pyrimidine with O-P(S)(OC$_2$H$_5$)$_2$ and O-P(S)(OC$_2$H$_5$)(C$_2$H$_5$) | 0.1<br>0.01 | 100<br>100 |
| (22) iso-$C_3H_7$-pyrimidine with O-P(S)(OC$_2$H$_5$)$_2$, Br, and O-P(S)(OC$_2$H$_5$)(C$_2$H$_5$) | 0.1<br>0.01 | 100<br>100 |

EXAMPLE 2

Myzus Test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica olearacea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed whereas 0% meant that none of the aphids were killed.

The active compounds, the concentrations of the active compound, the evaluation times and the results can be seen from Table 2.

Table 2
(Myzus test)

| Active compound | | Active compound concentration in % | Degree of destruction in % after 1 day |
|---|---|---|---|
| [(C$_2$H$_5$O)$_2$P(S)—O—C$_6$H$_4$—S—]$_2$ | (known) (D) | 0.1 | 0 |
| (C$_2$H$_5$O)$_2$P(S)—O—C$_6$H$_4$—S—C$_6$H$_4$—O—P(S)(OC$_2$H$_5$)$_2$ | (known) (C) | 0.1<br>0.01 | 100<br>0 |

Table 2-continued
(Myzus test)
| Active compound | | Active compound concentration in % | Degree of destruction in % after 1 day |
|---|---|---|---|
| 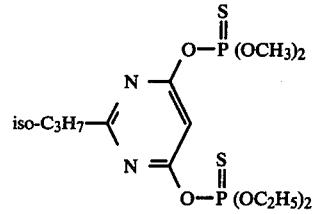 | (2) | 0.1<br>0.01 | 100<br>100 |
| 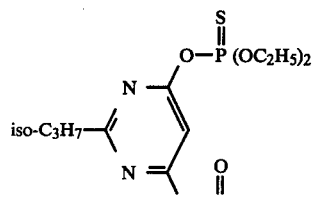 | (7) | 0.1<br>0.01 | 100<br>100 |
| 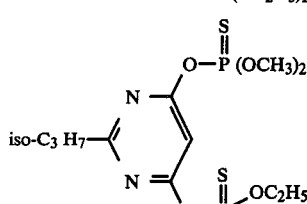 | (5) | 0.1<br>0.01 | 100<br>100 |
| 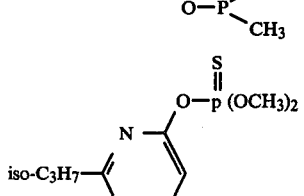 | (1) | 0.1<br>0.01 | 100<br>99 |
| 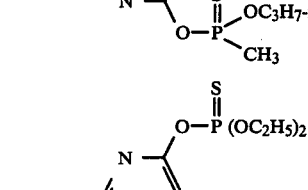 | (3) | 0.1<br>0.01 | 100<br>100 |
| 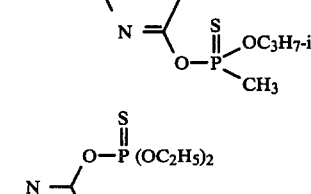 | (17) | 0.1<br>0.01 | 100<br>100 |
| 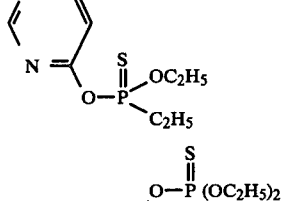 | (19) | 0.1<br>0.01 | 100<br>100 |

Table 2-continued (Myzus test)

| Active compound | | Active compound concentration in % | Degree of destruction in % after 1 day |
|---|---|---|---|
| [structure with iso-C₃H₇, pyrimidine, O-P(S)(OC₂H₅)₂ and O-P(S)(OC₂H₅)(C₂H₅)] | (8) | 0.1<br>0.01 | 100<br>100 |
| [structure with pyrimidine, O-P(S)(OC₂H₅)₂ and O-P(S)(OC₂H₅)(SC₃H₇-n)] | (16) | 0.1<br>0.01 | 100<br>100 |
| [structure with iso-C₃H₇, pyrimidine, O-P(S)(OC₂H₅)₂ and O-P(S)(OC₂H₅)(NH—C₃H₇-iso)] | (10) | 0.1<br>0.01 | 100<br>99 |
| [structure with iso-C₃H₇, pyrimidine, O-P(S)(OC₂H₅)(OC₃H₇-n) and O-P(S)(OC₃H₇-iso)(CH₃)] | (13) | 0.1<br>0.01 | 100<br>100 |
| [structure with iso-C₃H₇, pyrimidine, O-P(S)(OC₂H₅)(SC₃H₇-n) and O-P(S)(OC₃H₇-iso)(CH₃)] | (11) | 0.1<br>0.01 | 100<br>99 |
| [structure with iso-C₃H₇, pyrimidine, O-P(S)(OC₂H₅)(phenyl) and O-P(S)(OC₃H₇-iso)(CH₃)] | (12) | 0.1<br>0.01 | 100<br>100 |
| [structure with (CH₃)₂N, pyrimidine, O-P(S)(OC₂H₅)₂ and O-P(S)(OC₂H₅)(C₂H₅)] | (21) | 0.1<br>0.01 | 100<br>100 |

Table 2-continued
(Myzus test)

| Active compound | Active compound concentration in % | Degree of destruction in % after 1 day |
|---|---|---|
| Compound (20): diethoxy-pyrimidinyl bis-phosphorothioate structure with $C_2H_5O$–, N, N, O–P(=S)(OC$_2$H$_5$)$_2$ and O–P(=S)(OC$_2$H$_5$)(C$_2$H$_5$) | 0.1 <br> 0.01 | 100 <br> 100 |

EXAMPLE 3

Tetranychus Test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be see from Table 3:

Table 3
(Tetranychus test)

| Active compound | Active compound concentration in % | Degree of destruction in % after 2 days |
|---|---|---|
| $\{(C_2H_5O)_2 P(=S)-O-C_6H_4-S-\}_2$ (known) (D) | 0.1 | 0 |
| Compound (7): iso-$C_3H_7$-pyrimidine with O–P(=S)(OC$_2$H$_5$)$_2$ and O–P(=O)(OC$_2$H$_5$)$_2$ | 0.1 | 100 |
| Compound (5): iso-$C_3H_7$-pyrimidine with O–P(=S)(OCH$_3$)$_2$ and O–P(=S)(OC$_2$H$_5$)(CH$_3$) | 0.1 | 100 |
| Compound (1): iso-$C_3H_7$-pyrimidine with O–P(=S)(OCH$_3$)$_2$ and O–P(=S)(OC$_3$H$_7$-iso)(CH$_3$) | 0.1 | 99 |

Table 3-continued
(Tetranychus test)

| Active compound | Active compound concentration in % | Degree of destruction in % after 2 days |
|---|---|---|
| Compound (3): iso-C$_3$H$_7$-pyrimidine with O-P(=S)(OC$_2$H$_5$)$_2$ and O-P(=S)(OC$_3$H$_7$-iso)(CH$_3$) | 0.1 | 98 |
| Compound (17): pyrimidine with O-P(=S)(OC$_2$H$_5$)$_2$ and O-P(=S)(OC$_2$H$_5$)(C$_2$H$_5$) | 0.1 | 99 |
| Compound (8): iso-C$_3$H$_7$-pyrimidine with O-P(=S)(OC$_2$H$_5$)$_2$ and O-P(=S)(OC$_2$H$_5$)(C$_2$H$_5$) | 0.1 | 99 |
| Compound (16): pyrimidine with O-P(=S)(OC$_2$H$_5$)$_2$ and O-P(=S)(OC$_2$H$_5$)(SC$_3$H$_7$-n) | 0.1 | 95 |
| Compound (13): iso-C$_3$H$_7$-pyrimidine with O-P(=S)(OC$_2$H$_5$)(OC$_3$H$_7$-n) and O-P(=S)(OC$_3$H$_7$-iso)(CH$_3$) | 0.1 | 99 |
| Compound (11): iso-C$_3$H$_7$-pyrimidine with O-P(=S)(OC$_2$H$_5$)(SC$_3$H$_7$-n) and O-P(=S)(OC$_3$H$_7$-iso)(CH$_3$) | 0.1 | 100 |

Table 3-continued (Tetranychus test)

| Active compound | Active compound concentration in % | Degree of destruction in % after 2 days |
|---|---|---|
| [Structure (12): iso-C₃H₇-pyrimidine with O-P(=S)(OC₂H₅)(phenyl) and O-P(=S)(OC₃H₇-iso)(CH₃) substituents] | 0.1 | 100 |

EXAMPLE 4

Mosquito Larvae Test

Test insects: *Aëdes aegypti* larvae
Solvent: 99 parts by weight of acetone
Emulsifier: 1 part by weight of benzyl hydroxydiphenyl polyglycol ether To produce a suitable preparation of active compound, 2 parts by weight of the active compound were dissolved in 1,000 parts by volume of the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% meant that all the larvae were killed. 0% meant that no larvae at all were killed.

The active compounds, the concentrations of the active compounds, the test insects and the results can be seen from Table 4.

Table 4

(Mosquito larvae test/*Aëdes aegypti*)

| Active compound | Active compound concentration in % | Degree of destruction in % |
|---|---|---|
| [Structure (known) (B): (C₂H₅O)₂P(=S)—O—pyrimidine with CH₃ and C₃H₇-iso] | 1.0 / 0.1 | 100 / 0 |
| [Structure (2): iso-C₃H₇-pyrimidine with O-P(=S)(OCH₃)₂ and O-P(=S)(OC₂H₅)₂] | 0.01 | 100 |
| [Structure (7): iso-C₃H₇-pyrimidine with O-P(=S)(OC₂H₅)₂ and O-P(=O)(OC₂H₅)₂] | 0.1 | 100 |
| [Structure (1): iso-C₃H₇-pyrimidine with O-P(=S)(OCH₃)₂ and O-P(=S)(OC₃H₇-iso)(CH₃)] | 0.01 | 100 |
| [Structure (3): iso-C₃H₇-pyrimidine with O-P(=S)(OC₂H₅)₂ and O-P(=S)(OC₃H₇-iso)(CH₃)] | 0.1 | 100 |
| [Structure (8): iso-C₃H₇-pyrimidine with O-P(=S)(OC₂H₅)₂ and O-P(=S)(OC₂H₅)(C₂H₅)] | 0.1 | 100 |

Table 4-continued
(Mosquito larvae test/Aëdes aegypti)

| Active compound | Active compound concentration in % | Degree of destruction in % |
|---|---|---|
| (17) | 0.1 | 100 |
| (13) | 0.1 | 100 |
| (12) | 0.1 | 100 |
| (15) | 0.1 | 100 |
| (9) | 0.1 | 100 |
| (10) | 0.1 | 100 |
| (4) | 0.1 | 100 |
| (11) | 0.1 | 100 |
| (16) | 0.1 | 100 |

The process of the present invention is illustrated in the following preparative examples:

EXAMPLE 5

(a) The O-[6-hydroxy-pyrimidin(4)yl]-(thiono)(thiol)-phosphoric(phosphonic) acid esters and ester-amides to be used as starting materials could be prepared, for example, as follows:

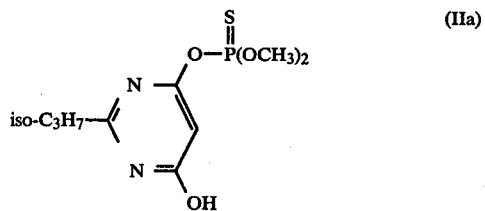

A mixture of 18.4 g (0.12 mol) of 2-isopropyl-4,6-dihydroxypyrimidine, 12.5 g (0.125 mol) of triethylamine and 60 ml of methylene chloride was stirred for 1 hour at room temperature. It was then cooled to about 5° C. and 16 g (0.1 mol) of O,O-dimethyl-thionophosphoric acid diester chloride were added dropwise at this temperature. Thereafter the reaction mixture was stirred for 20 hours at room temperature and then filtered, and the filtrate was evaporated in vacuo. The residue was triturated with water and the crystalline product was filtered off. 22.7 g (82% of theory) of O,O-dimethyl-O-[2-isopropyl-6-hydroxypyrimidin(4)yl]-thionophosphoric acid ester were thus obtained in the form of colorless crystals of melting point 123° C.

The following compounds of the formula

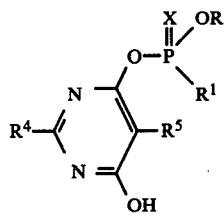
(II), could be prepared analogously:

17.3 g (0.1 mol) of O-isopropyl-methane-thionophosphonic acid ester chloride were added dropwise to a mixture of 27.8 g (0.1 mol) of O,O-dimethyl-O-[2-isopropyl-6-hydroxypyrimidin(4)yl]-thionophosphoric acid ester, 20.7 g (0.15 mol) of potassium carbonate and 300 ml of acetonitrile. The reaction mixture was stirred for a further hour at 45° C. and was then poured into 400 ml of toluene. The toluene solution was washed twice with 300 ml of water at a time and was dried over sodium sulfate. The solvent was then stripped off in vacuo and the residue was subjected to slight distillation. This gave 28.8 g (70% of theory) of O-isopropyl-O-[2-isopropyl-4-dimethoxy-thionophosporyloxypyrimidin(6)yl]-methane-thionophosphoric acid ester in the form of a yellow oil having a refractive index $n_D^{27}$ of 1.5165.

The following compounds of the formula

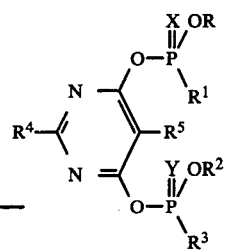
I,

Table 5

| Compound II | R | $R^1$ | $R^4$ | $R^5$ | X | Yield (% of theory) | Physical data (refractive index melting point, °C.) |
|---|---|---|---|---|---|---|---|
| (b) | —$C_2H_5$ | —$OC_2H_5$ | —$C_3H_{7\text{-}iso}$ | H | S | 98 | 94 |
| (c) | —$CH_3$ | —$OCH_3$ | H | H | S | 9 | 148 |
| (d) | —$C_2H_5$ | —$OC_2H_5$ | —$SCH_3$ | H | S | 35 | 110 |
| (e) | —$C_2H_5$ | —$OC_2H_5$ | H | H | S | 26 | 83 |
| (f) | —$C_3H_7\text{-}iso$ | —$CH_3$ | —$C_3H_7\text{-}iso$ | H | S | 18 | 136 |
| (g) | —$C_2H_5$ | —$C_2H_5$ | —$C_3H_7\text{-}iso$ | H | S | 52 | 88 |
| (h) | —$C_2H_5$ | —$OC_3H_7\text{-}n$ | —$C_3H_7\text{-}iso$ | H | S | 60 | $n_D^{23}$:1.5168 |
| (i) | —$C_2H_5$ | —$SC_3H_7\text{-}n$ | —$C_3H_7\text{-}iso$ | H | S | 63 | $n_D^{23}$:1.5479 |
| (j) | —$C_2H_5$ | —C6H5(phenyl) | —$C_3H_7\text{-}iso$ | H | S | 75 | 116 |
| (k) | —$C_2H_5$ | —$OC_2H_5$ | —$OC_2H_5$ | H | S | 20 | 101 |
| (l) | —$C_2H_5$ | —$OC_2H_5$ | —$C_3H_7\text{-}iso$ | Br | S | 43 | 117 |
| (m) | —$C_2H_5$ | —$OC_2H_5$ | —$N(CH_3)_2$ | H | S | 20 | 132 |
| (n) | —$C_2H_5$ | —$OC_2H_5$ | —$CH_3$ | H | S | 7 | 79 |
| (o) | —$C_2H_5$ | —$OC_2H_5$ | —C6H5(phenyl) | H | S | 12 | 118 |
| (p) | —$C_2H_5$ | —$OC_2H_5$ | —$C_3H_7\text{-}iso$ | $CH_3$ | S | 48 | 103 |

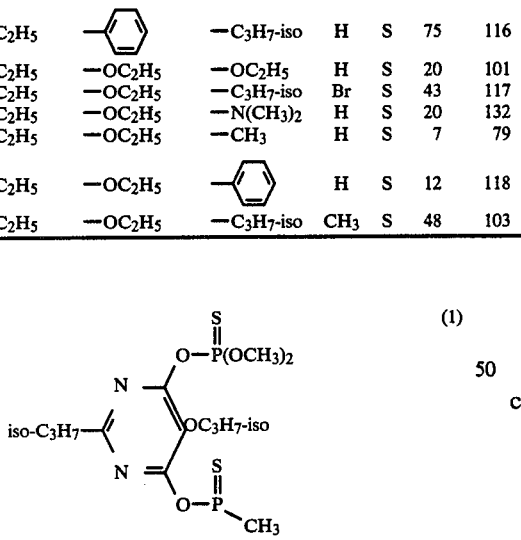
(1)

could be prepared analogously:

Table 6

| Compound No. | R | $R^1$ | $R^2$ | $R^3$ | $R^4$ | $R^5$ | X | Y | Yield (% of theory) | Physical data (refractive index) |
|---|---|---|---|---|---|---|---|---|---|---|
| 2 | —$C_2H_5$ | —$OC_2H_5$ | $CH_3$— | $CH_3$— | —$C_3H_7\text{-}iso$ | H | S | S | 60 | $n_D^{24}$: 1.5080 |
| 3 | —$C_2H_5$ | —$OC_2H_5$ | iso-$C_3H_7$— | $CH_3$— | —$C_3H_7\text{-}iso$ | H | S | S | 71 | $n_D^{24}$: 1.5095 |
| 4 | —$C_2H_5$ | —$OC_2H_5$ | $C_2H_5$— | n-$C_3H_7S$— | —$C_3H_7\text{-}iso$ | H | S | S | 87 | $n_D^{22}$: 1.5253 |
| 5 | —$CH_3$ | —$OCH_3$ | $C_2H_5$— | $CH_3$— | —$C_3H_7\text{-}iso$ | H | S | S | 36 | $n_D^{22}$: 1.5226 |
| 6 | —$CH_3$ | —$OCH_3$ | $C_2H_5$— | C6H5(phenyl) | —$C_3H_7\text{-}iso$ | H | S | S | 42 | $n_D^{22}$: 1.5590 |
| 7 | —$C_2H_5$ | —$OC_2H_5$ | $C_2H_5$— | $C_2H_5O$— | —$C_3H_7\text{-}iso$ | H | S | O | 72 | $n_D^{22}$: 1.4918 |

Table 6-continued

| Compound No. | R | R$^1$ | R$^2$ | R$^3$ | R$^4$ | R$^5$ | X | Y | Yield (% of theory) | Physical data (refractive index) |
|---|---|---|---|---|---|---|---|---|---|---|
| 8 | —C$_2$H$_5$ | —OC$_2$H$_5$ | C$_2$H$_5$— | C$_2$H$_5$— | —C$_3$H$_7$-iso | H | S | S | 84 | n$_D^{22}$: 1.5124 |
| 9 | —C$_2$H$_5$ | —OC$_2$H$_5$ | C$_2$H$_5$— |  | —C$_3$H$_7$-iso | H | S | S | 84 | n$_D^{22}$: 1.5442 |
| 10 | —C$_2$H$_5$ | —OC$_2$H$_5$ | C$_2$H$_5$— | iso-C$_3$H$_7$—NH— | —C$_3$H$_7$-iso | H | S | S | 82 | n$_D^{22}$: 1.5122 |
| 11 | —C$_3$H$_7$-iso | —CH$_3$ | C$_2$H$_5$— | C$_3$H$_7$S— | —C$_3$H$_7$-iso | H | S | S | 78 | n$_D^{22}$: 1.5325 |
| 12 | —C$_3$H$_7$-iso | CH$_3$ | C$_2$H$_5$— |  | —C$_3$H$_7$-iso | H | S | S | 72 | n$_D^{22}$: 1.5498 |
| 13 | —C$_2$H$_5$ | —OC$_3$H$_7$-n | iso-C$_3$H$_7$— | CH$_3$— | —C$_3$H$_7$-iso | H | S | S | 79 | n$_D^{20}$: 1.5088 |
| 14 | —C$_2$H$_5$ | —SC$_3$H$_7$-n | C$_2$H$_5$— | 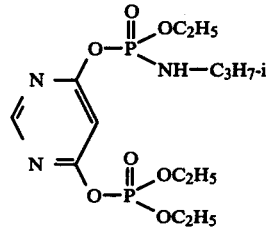 | —C$_3$H$_7$-iso | H | S | S | 77 | n$_D^{20}$: 1.5653 |
| 15 | —C$_2$H$_5$ | 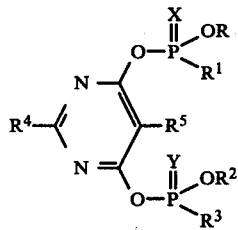 | C$_2$H$_5$— | C$_2$H$_5$— | —C$_3$H$_7$-iso | H | S | S | 80 | n$_D^{20}$: 1.5561 |
| 16 | —C$_2$H$_5$ | —OC$_2$H$_5$ | C$_2$H$_5$— | n-C$_3$H$_7$S— | H | H | S | S | 77 | n$_D^{22}$: 1.5341 |
| 17 | —C$_2$H$_5$ | —OC$_2$H$_5$ | C$_2$H$_5$— | C$_2$H$_5$— | H | H | S | S | 75 | n$_D^{22}$: 1.5205 |
| 18 | —C$_2$H$_5$ | —OC$_2$H$_5$ | C$_2$H$_5$— | n-C$_3$H$_7$H$_7$S— | H | H | S | S | 80 | n$_D^{22}$: 1.5551 |
| 19 | —C$_2$H$_5$ | —OC$_2$H$_5$ | C$_2$H$_5$— | C$_2$H$_5$— | —SCH$_3$ | H | S | S | 78 | n$_D^{22}$: 1.5465 |
| 20 | —C$_2$H$_5$ | —OC$_2$H$_5$ | C$_2$H$_5$— | C$_2$H$_5$— | —OC$_2$H$_5$ | H | S | S | 81 | n$_D^{20}$: 1.5191 |
| 21 | —C$_2$H$_5$ | —OC$_2$H$_5$ | C$_2$H$_5$— | C$_2$H$_5$— | —N(CH$_3$)$_2$ | H | S | S | 82 | n$_D^{22}$: 1.5359 |
| 22 | —C$_2$H$_5$ | —OC$_2$H$_5$ | C$_2$H$_5$— | C$_2$H$_5$— | —C$_3$H$_7$-iso | Br | S | S | 78 | n$_D^{20}$: 1.5285 |
| 23 | —C$_2$H$_5$ | —OC$_2$H$_5$ | C$_2$H$_5$— | C$_2$H$_5$— | —C$_3$H$_7$-iso | CH$_3$ | S | S | 75 | n$_D^{24}$: 1.5110 |

Similarly there can be prepared

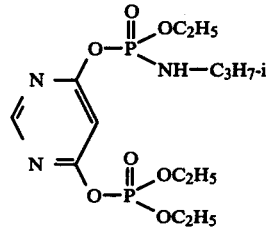

and the like.

It will be appreciated that the instant specification and examples are set forth by way of illustration and not limitation, and that various modifications and changes may be made without departing from the spirit and scope of the present invention.

What is claimed is:

1. An O,O'-dialkyl-4,6-diphosphorylated pyrimidine of the formula

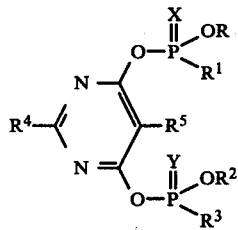 (I), in which

R and R$^2$ each independently is alkyl with 1 to 4 carbon atoms,

R$^1$ and R$^3$ each independently is alkyl, alkoxy, alkylthio or alkylamino each with 1 to 4 carbon atoms per alkyl radical, or phenyl, R$^4$ is hydrogen, alkyl with 1 to 4 carbon atoms, or alkoxy, alkylthio or dialkylamino each with 1 to 3 carbon atoms per alkyl radical, R$^5$ is hydrogen, halogen or alkyl with 1 to 3 carbon atoms, and X and Y each independently is oxygen or sulfur, with the proviso that $$-\overset{\overset{X}{\|}}{P}\overset{OR}{\underset{R^1}{\diagup}}$$

is different from $$-\overset{\overset{X}{\|}}{P}\overset{OR^2}{\underset{R^3}{\diagup}}$$

2. A compound according to claim 1, in which R and R$^2$ each independently is alkyl with 1 to 4 carbon atoms, R$^1$ and R$^3$ each independently is alkyl, alkoxy, alkylthio or monoalkylamino with in each case 1 to 4 carbon atoms or phenyl, R$^4$ is hydrogen, alkyl with 1 to 4 carbon atoms, or alkoxy, alkylthio or dialkylamino each with 1 to 3 carbon atoms per alkyl radical, R$^5$ is hydrogen, chlorine, bromine or alkyl with 1 to 3 carbon atoms and X and Y each is sulfur.

3. The compound according to claim 1, wherein such compound is O-isopropyl-O-[2-isopropyl-4-dimethoxy-thionophosphoryloxypyrimidin(6)yl]-methane-thionophosphonic acid ester of the formula

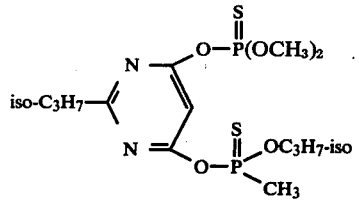

4. The compound according to claim 1, wherein such compound is O,O-dimethyl-O-[2-isopropyl-4-diethoxy-thionophosphoryloxy-pyrimidin(6)yl]-thionophosphoric acid ester of the formula

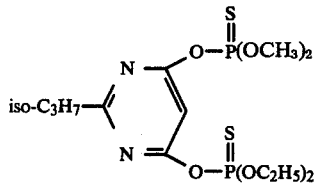

5. The compound according to claim 1, wherein such compound is O-isopropyl-O-[2-isopropyl-4-diethoxy-thionophosphoryloxy-pyrimidin(6)yl]-methane-thionophosphonic acid ester of the formula

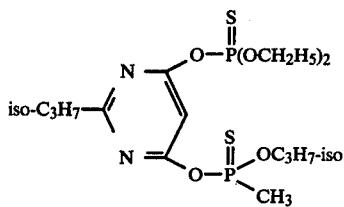

6. The compound according to claim 1, wherein such compound is O,O-diethyl-O-[2-isopropyl-4-diethoxy-phosphoryloxy-pyrimidin(6)yl]-thionophosphroic acid ester of the formula

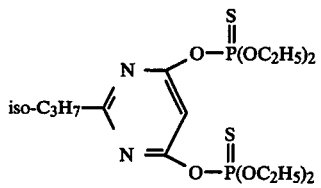

7. The compound according to claim 1, wherein such compound is O-ethyl-O-[2-isopropyl-4-diethoxy-thionophosphoryloxy-pyrimidin(6)yl]-ethane-thionophosphonic acid ester of the formula

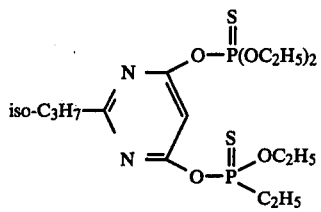

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9, in which said compound is
O-isopropyl-O-[2-isopropyl-4-dimethoxy-thionophosphoryloxypyrimidin(6)yl]-methane-thionophosphonic acid ester,
O,O-dimethyl-O-[2-isopropyl-4-diethoxy-thionophosphoryloxy-pyrimidin(6)yl]-thionophosphoric acid ester,
O-isopropyl-O-[2-isopropyl-4-diethoxy-thionophosphoryloxy-pyrimidin(6)yl]-methane-thionophosphonic acid ester.
O,O-diethyl-O-[2-isopropyl-4-diethoxyphosphoryloxy-pyrimidin(6)yl]-thionophosphoric acid ester, or
O-ethyl-O-[2-isopropyl-4-diethoxy-thionophosphoryloxy-pyrimidin(6)yl]-ethane-thionophosphonic acid ester.

* * * * *